United States Patent
Grudin et al.

(10) Patent No.: US 10,835,154 B2
(45) Date of Patent: Nov. 17, 2020

(54) METHOD AND APPARATUS FOR MEASURING AIRWAY RESISTANCE AND LUNG COMPLIANCE

(71) Applicant: Oleg Grudin, Montreal (CA)

(72) Inventors: Oleg Grudin, Montreal (CA); Victor Lopata, Kiev (UA)

(73) Assignee: SPIRO-TECH MEDICAL INC., Montreal (CA)

( * ) Notice: Subject to any disclaimer, the term of this patent is extended or adjusted under 35 U.S.C. 154(b) by 610 days.

(21) Appl. No.: 15/095,489

(22) Filed: Apr. 11, 2016

(65) Prior Publication Data

US 2016/0256073 A1    Sep. 8, 2016

Related U.S. Application Data

(63) Continuation of application No. PCT/CA2014/051073, filed on Nov. 6, 2014.

(60) Provisional application No. 61/900,964, filed on Nov. 6, 2013.

(51) Int. Cl.
*A61B 5/085*    (2006.01)
*A61B 5/087*    (2006.01)
*A61B 5/00*    (2006.01)

(52) U.S. Cl.
CPC .............. *A61B 5/085* (2013.01); *A61B 5/087* (2013.01); *A61B 5/7278* (2013.01); *A61B 5/7282* (2013.01)

(58) Field of Classification Search
None
See application file for complete search history.

(56) References Cited

U.S. PATENT DOCUMENTS

| | | | |
|---|---|---|---|
| 4,259,967 A | 4/1981 | Vooren et al. | |
| 4,802,492 A | 2/1989 | Grunstein | |
| 5,233,998 A * | 8/1993 | Chowienczyk | A61B 5/085 600/533 |
| 5,314,690 A * | 5/1994 | Patterson | A61K 38/046 424/114 |
| 5,634,471 A | 6/1997 | Fairfax et al. | |
| 6,631,716 B1 | 10/2003 | Robinson et al. | |
| 6,718,975 B2 | 4/2004 | Blomberg | |
| 2003/0100843 A1* | 5/2003 | Hoffman | A61B 5/0809 600/538 |

(Continued)

FOREIGN PATENT DOCUMENTS

| | | |
|---|---|---|
| WO | WO 2009/013155 A2 | 1/2009 |
| WO | WO 2013/098714 A1 | 7/2013 |
| WO | WO 2015/005958 A1 | 1/2015 |

OTHER PUBLICATIONS

Kapp et al. (The Shape of the Maximum Expiratory Flow Volume Curve; Chest 1988; 94:799-8(6).*

(Continued)

*Primary Examiner* — Kaylee R Wilson
*Assistant Examiner* — Jay B Shah
(74) *Attorney, Agent, or Firm* — Anglehart et al.

(57) ABSTRACT

Measurement of airway resistance and/or lung compliance during non forced exhalation is performed using initial occlusion of exhalation followed by removal of the occlusion or opening of a shutter. The measurement device can use a single sensor to measure both pressure and flow. A pressure monitor can detect that exhalation is improperly forced to signal an error or to reject a pressure and flow measurement from a forced exhalation trial.

20 Claims, 10 Drawing Sheets

(56) References Cited

U.S. PATENT DOCUMENTS

| | | | |
|---|---|---|---|
| 2003/0140925 A1 | 7/2003 | Sapienza et al. | |
| 2004/0230108 A1* | 11/2004 | Melker | A61B 5/0873 600/340 |
| 2004/0249300 A1 | 12/2004 | Miller | |
| 2008/0139956 A1* | 6/2008 | Diong | A61B 5/085 600/533 |
| 2008/0178880 A1* | 7/2008 | Christopher | A61M 16/0051 128/204.23 |
| 2010/0286548 A1* | 11/2010 | Lazar | A61B 5/087 600/538 |
| 2011/0201958 A1 | 8/2011 | Lazar et al. | |
| 2011/0282228 A1 | 11/2011 | Shiner et al. | |
| 2012/0161256 A1* | 6/2012 | Grudin | G01F 1/6842 257/415 |
| 2014/0276173 A1 | 9/2014 | Banner et al. | |
| 2014/0309546 A1 | 10/2014 | Fazzi et al. | |

OTHER PUBLICATIONS

Gritti et al. (A new approach to the determination of airway resistance: interrupter technique vs. plethysmography; J Bras Pneumol. 2011;37(1):61-68).*

Schmalisch et al.; Differences in tidal breathing between infants with chronic lung diseases and healthy controls; BMC Pediatrics 2005, 5:36 (Year: 2005).*

Hage et al.; Detection of flow limitation during tidal breathing by the interruptor technique; Eur Respir J, 1995, 8, 1910-1914 (Year: 1995).*

Klaas et al., The opening interruptor a new variant of a technique for measuring repiratory, EUR J Respir Dis, 1982, 63, 449-458.

M. Gappa et al., Passive respiratory mechanics: the occlusion techniques, European Respiratory Journal 2001 17: 141-148.

Ireneusz Jab•o• ski et al, A Complex Mathematical Model of the Respiratory System as a Tool for the Metrological Analysis of the Interrupter Technique, XIX IMEKO World Congress Fundamental and Applied Metrology Sep. 6-11, 2009, Lisbon, Portugal.

PCT/CA2014/051073 IPRP with related claims.

PCT/CA2014/051073 ISR.

PCT/CA2014/051073 written opinion.

EP appl. 14859763 search report dated May 23, 2018.

G Burns et al., A novel hypothesis to explain the bronchconstrictor effect of deep inspiration in asthma, Thorax. Feb. 2002; 57(2): 116-119.

Chinese application 201480084526.0 Office Action dated Sep. 17, 2019.

Chinese application 201480084526.0 Office Action dated Sep. 17, 2019—English translation.

* cited by examiner

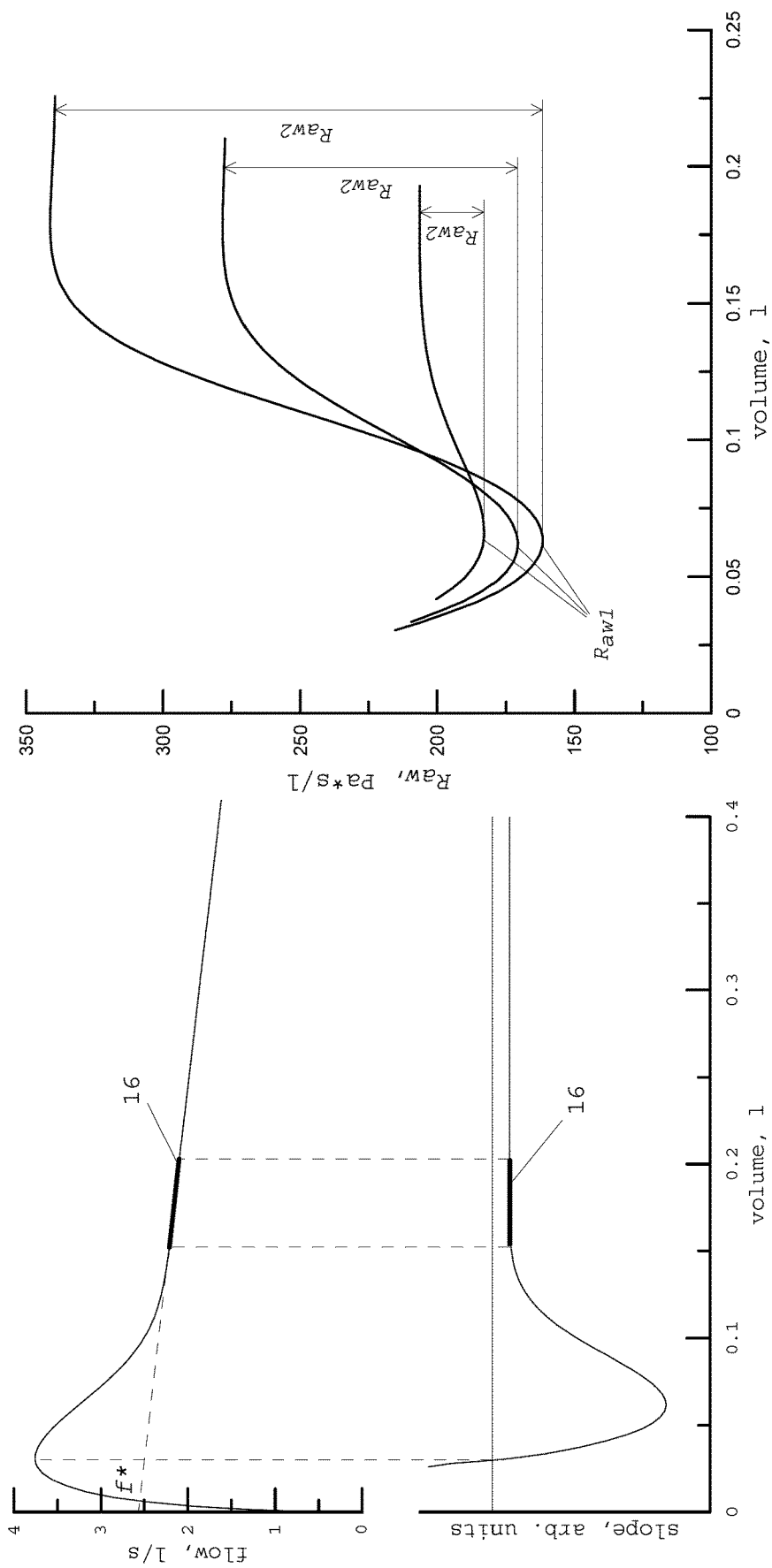

METHOD AND APPARATUS FOR MEASURING AIRWAY RESISTANCE AND LUNG COMPLIANCE

This application claims priority of U.S. provisional patent application 61/900,964, filed Nov. 6, 2013.

TECHNICAL FIELD

The present application relates to medical diagnostics devices, more particularly to devices that measure respiratory parameters such as airway resistance and lung compliance.

BACKGROUND

Respiratory parameters are often measured to monitor and diagnose the progression of respiratory diseases and to generate therapeutic recommendations. It may be beneficial to use data on airway resistance and compliance to determine and prescribe appropriate treatment for individuals who have been exposed to smoke, biological or chemical substances or suffering from chronic lung diseases.

Several techniques are available to measure airway resistance. The technique of forced oscillations measures total respiratory resistance and requires high level of expertise of medical personnel. Body plethysmography measures airway resistance, but it requires large apparatus and is not easy to use.

The so-called interrupter or shutter measuring method provides alternative way of determining airway resistance which requires minimal cooperation of the subject. With this method, the subject breathes through a breathing tube. In a first step the flow through the breathing tube is measured. In a second step the opening of the breathing tube is briefly closed by a shutter. Within a short period of time (typically from 20 ms to 150 ms) after closing, air pressure in the mouth and breathing tube increases to the level which is supposed to correspond alveolar pressure at the moment of air flow interruption. Measured values of air flow and built-up pressure are used for determination of airway resistance. Usually air flow interruption is repeated several times during the test synchronously with the subject's breathing.

One variant of the interruption technique known as "opening" interruption method uses a different sequence of measurements. The flow rate is measured not before the interruption of air flow, but shortly after opening of the shutter. In this method, a longer period of interruption provides more complete equilibrium between alveolar and mouth pressure which improves accuracy of airway resistance measurement. In accordance with this method, interruptions are made only during inspiration and in the middle part of the inspiratory phase. Mouth pressure is measured immediately before opening while air flow is averaged during the period of 15-35 ms after opening of the shutter.

Integration of a flowmeter with a shutter used to measure peak expiratory flow (PEF) after the end of occlusion is known from the U.S. Pat. No. 5,634,471 to Fairfax et al. In accordance with this invention, the subject performs forced expiration through the device with initially closed distal end of the flow tube. The proposed breathing maneuver includes a short phase of pressure build-up inside the flow tube limited to approximately 200 ms after which the shutter is automatically opened even if pressure has not reached preset shutter opening threshold. It is claimed that ratio of air pressure immediately before the end of occlusion and peak flow is equivalent to airway resistance.

Muscles are used to move the lung and chest wall for inspiration, and forced expiration additionally uses abdominal wall muscles. Passive expiration or resting exhalation is a process involving the recoil of the lungs and rib cage from some stage of inspiration (greater following a full inspiration) due to stored elastic energy. In normal breathing during regular activity, only passive expiration is used.

A drawback of the method taught in Fairfax et al stems from the fact that extreme muscular efforts associated with forced expiration lead to high intra-thoracic pressure and narrowing of small airways and may even cause their collapse resulting in essentially different distribution of airways resistance across bronchial tree compared to its normal conditions at quiet breathing.

The respiration maneuver described in U.S. Pat. No. 5,634,471 has a normally high opening pressure of the shutter (10 to 20 kPa), typical of forced expiration, that defines high peak flow which can reach and exceed 50 l/s for the subject with airway resistance of say 200 Pa*s/l. Such a peak flow empties the lungs very quickly. Accurate measurement of such high flow is a technically challenging problem. In addition to this, detailed analysis of peak flow waveform needed for determining of lung parameters such as compliance becomes problematic due to imposing of forced expiration waveform which is supposed to be generated by the subject.

SUMMARY

Applicants have discovered that unforced expiration can be used to obtain an accurate and repeatable measurement of airway resistance and/or compliance when such unforced expiration is initially blocked by a shutter and then unforced expiration is allowed to follow its course. The onset of unforced expiration begins with a relaxation of the chest wall muscles that allows the recoil of the lungs and rib cage to build up air pressure. With the shutter closed, this pressure stabilizes (or approaches to be the same at the mouth as in the lungs and bronchial tree. When the shutter opens, the air flow develops a peak value greater than a peak associated with normal relaxed expiration, and thereafter unforced expiration follows its usual course and flow. The stable pressure when the shutter is closed represents the stored elastic energy which varies in accordance with the patient's level of inspiration and pulmonary condition. The peak flow value following release of the shutter corresponds inversely to the airway resistance of the bronchia without substantial compression due to muscles acting to force expiration and to the stable pressure prior to shutter release.

Applicants have found that an apparatus can be configured to detect or to discriminate unforced from forced expiration, and to use such detection to signal when a measurement is based on forced expiration and is thus erroneous, or to suppress the measurement.

Applicants have also found that an apparatus can be provided with a single pressure sensor that measures positive pressure in a breathing tube relative to ambient pressure when a shutter is closed and, when the shutter is opened, that measures expiration flow in the breathing tube by measuring negative pressure relative to ambient caused by expiration flow. This has the advantage that both the pressure measurement and the flow measurement are based on the same sensor, and since airway resistance is a quotient of these measurements, the stability of the sensor sensitivity is less important. This pressure sensor used in the measurements can be, for example, a calorimetric type micro-flow sensor.

The object of the present invention is to simplify the testing procedure, thus minimizing the need for the subject's cooperation, shorten testing time and/or determine medically valuable information on distribution of airways resistance across the bronchial tree. Another object is to simplify the design of the respiratory device, reduce its size and/or improve the accuracy of the measurements.

According to the present invention, the subject keeps a breathing tube in his/her mouth, the proximal end of the tube being tightly wrapped with lips. The coupling with the patient's mouth can be the end of the tube directly (i.e. an integrated mouthpiece) or a mouthpiece as desired. Distal end of the breathing tube is initially tightly closed with the shutter. After the subject starts to exhale without forcing, pressure in the closed breathing tube increases reaching certain threshold after which the shutter rapidly opens the tube. The threshold can be simply a fixed level, and is preferably either a fixed level for a predetermined time, or a deceleration of pressure increase, that indicate stabilization of pressure. Pressure inside the breathing tube drops to nearly ambient pressure and air flow through the tube reaches its maximum value shortly after the shutter opening and then reduces. The time of unforced expiration remains substantially the same whether the device is used or not. Assuming that alveolar pressure equals pressure inside the breathing tube at the instance of the shutter opening, airway resistance can be determined from air flow waveform.

Lung compliance is determined from the rate of air flow decrease after reaching maximum peak value.

The difference between the proposed respiration maneuver and those from prior art interruption techniques is that measurement starts with occlusion when the subject begins relaxed exhalation into the breathing tube closed by the shutter. During occlusion, exhalation is performed slowly, without forced efforts. Preferable duration of occlusion is 0.3-1 ls, namely a time period which is long enough to equalize alveolar and mouth pressure. No synchronization of the shutter opening with breathing cycle is needed. Because the pressure should be stabilizing in the lungs and breathing tube when the shutter is closed, there is little urgency to open the shutter, for example, it is possible to wait, for example 100 ms to around 1000 ms, before releasing the shutter. Opening can be automatically initiated by increased build-up pressure exceeding predetermined threshold. After the end of occlusion, the subject continues to exhale quietly without forcing exhalation and can slowly stop relaxed exhalation naturally in about 0.5-5 s after opening of the shutter. Opening pressure is set to a level high enough to cause post-opening flow spike essentially exceeding quiet exhalation flow.

BRIEF DESCRIPTION OF THE DRAWINGS

The invention will be better understood by way of the following detailed description of embodiments of the invention with reference to the appended drawings, in which:

FIG. 9 illustrates procedure of calculation of interception flow f* from flow-volume waveform and its slope.

FIG. 10 presents Raw as function of exhaled volume.

DETAILED DESCRIPTION

Figure 1:
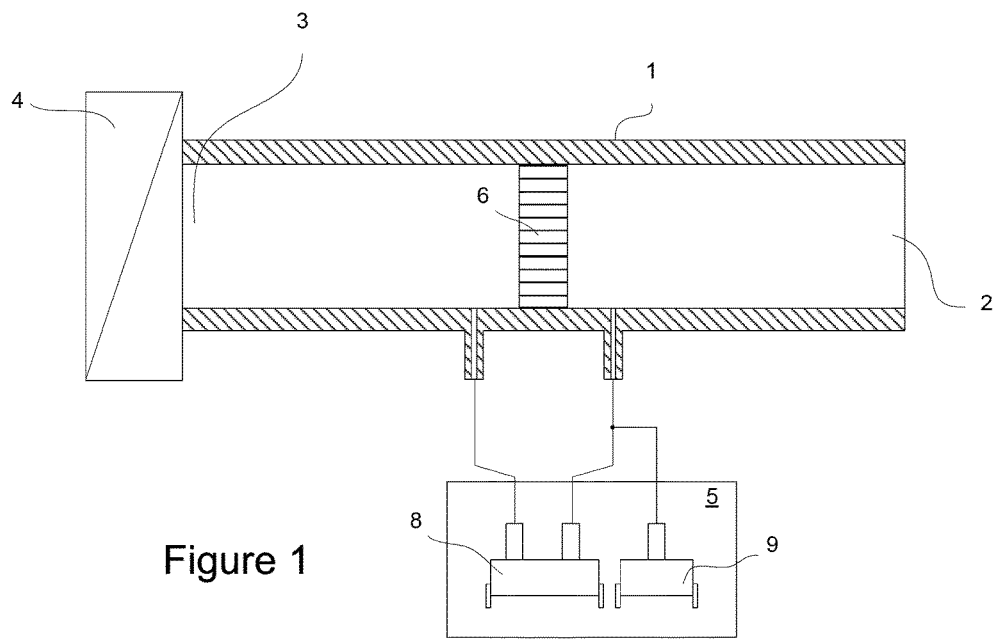
FIG. 1 shows general scheme of the respiratory device for airway resistance measurement.

One of possible embodiments of the respiratory device is illustrated in FIG. 1. The flowmeter contains the breathing tube 1 with proximal 2 and distal 3 ends. The shutter 4 is attached to the distal end 3 of the tube. Air flow through the tube and pressure inside the tube are measured by the transducer 5. The flowmeter contains a functional element 6 which generates differential pressure as function of air flow. Such an element may alternatively be for example Pitot tube or orifice, or other type of known flow restrictors such as those used in Fleisch or Lilly pneumotachometers.

The transducer 5 may include one sensor 8 to measure pressure differential across functional element 6 and second sensor 9 to measure pressure inside the tube 1. It is also possible to use only one pressure sensor to measure both pressure caused by air flow and pressure inside the tube 1 which will be described below.

In accordance with the proposed testing procedure, the subject produces quiet exhalation through the breathing tube 1 without applying forced efforts. The flow waveform during quiet exhalation in the case of a permanently opened shutter is shown schematically in FIG. 2 by a dashed line. Typical maximum air flow during quiet expiration is less than or about 1 l/s.

Figure 2:
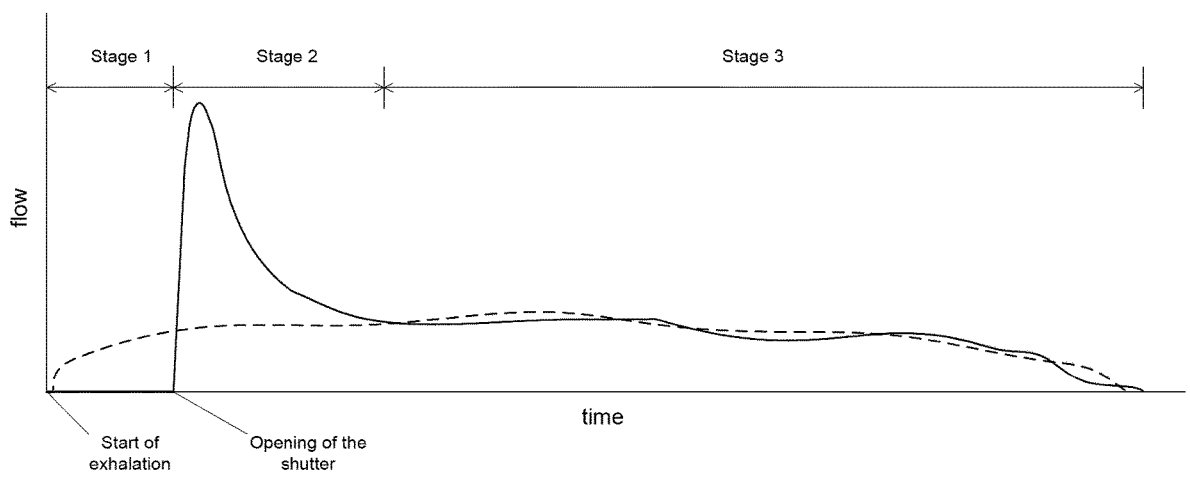
FIG. 2 presents schematically flow waveforms during quiet exhalation through the opened flow tube and the tube with initially closed shutter.

The solid line in FIG. 2 depicts flow waveform during exhalation through the breathing tube 1 with the shutter 4 initially closed. In stage 1 (occlusion) between the start of exhalation and opening of the shutter 4, flow through the breathing tube 1 is zero, and air inside lung is being compressed resulting in a mouth pressure increase (see FIG. 2).

As described above, the subject can start to exhale without forcing, and pressure in the closed breathing tube can increase, thus reaching a certain level determined by the relaxation of the breathing muscles and the state of inhalation. The opening of the shutter can be done when pressure reaches this level. Detection of this level or the approach to this level can be done using a pressure sensor and control electronics, however, in some cases, manual release of the shutter can be used. The subject can be instructed to release the shutter when he or she has relaxed breathing muscles while maintaining a seal at the mouthpiece. This can be easy to self-regulate for the subject. It will be appreciated that the shutter opening pressure can also be set to be a bit higher, thus causing the subject to exert a bit of force for the purposes of triggering the shutter, as long as the subsequent exhalation is not forced. An advantage of setting the opening pressure higher than the normal static pressure of the relaxed breathing muscles is that a single fixed set point can be used, thus simplifying electronic control, and at least in some cases, a moderately higher occlusion pressure can provide better peak flow signal. A disadvantage is that the subject's cooperation to use only temporary force plays a role in the measurement. Forced exhalation, as mentioned above, adversely affects the lungs and disturbs measurement of airway resistance when the force is too great. It also can impede the ability to measure characteristics from the flow curve shape, as this depends on forced exhalation muscle control by the subject.

Stage 2 starts with opening of the shutter 4. At this stage, air flow reaches a peak value at time $t_p$ after the shutter 4 opening and then decreases. The shape of the air flow waveform depends in general on airway resistance and the elastic properties of lung tissue, airways and thoracic wall. The typical duration of stage 2 is about 100-300 ms with peak flow time $t_p$ of 15-30 ms.

Stage 3 covers the rest of exhalation maneuver and does not differ essentially from quiet exhalation through the opened tube (dashed line). This stage is not important for measurement purposes, and the subject can slowly stop exhalation (without rapid interruption) in about 0.5-1 s after shutter opening without affecting measurement.

The flow waveform caused by air compression inside the chest and subsequent rapid opening of the shutter 4, is imposed on normal non-forced exhalation of the subject. It is preferable to create test conditions when such a waveform is clearly distinguishable from quiet exhalation.

For this purpose, the subject must not apply forced efforts, and instead perform quiet, relaxed exhalation. It is also important to design the shutter such that its opening occurs at a pressure $P_{max}$ high enough to create a significant flow peak. In most patients, this is not a problem since the relaxation of the chest wall muscles allows the recoil of the lungs and rib cage to build up sufficient air pressure. Assuming that airway resistance varies usually from 150 Pa*s/l to 450 Pa*s/l, a reasonable value for $P_{max}$ is about 900 Pa that results in 2-6 l/s peak flow clearly distinguishable from quiet expiration flow. In general, a shutter opening pressure $P_{max}$ can be from 500 Pa to 2000 Pa for the proposed method which does not create serious inconvenience for the subject during the test.

For example, at the beginning of the test when the shutter 4 is closed, air inside the breathing tube and upper levels of respiratory tract is being compressed slowly. To increase pressure from atmospheric pressure $P_{atm}$ to $P_{atm}+P_{max}$, volume of air $\Delta V$ must be delivered from lung:

$$\Delta V = \frac{P_{max} V_{comp}}{P_{atm}}, \tag{1}$$

where $V_{comp}$ is internal volume of the breathing tube and upper levels of respiratory tract.

Average air flow through the respiratory tract needed to deliver such amount of air during compression time $t_{comp}$ of approximately 1 second can be estimated as:

$$f_1 = \frac{\Delta V}{t_{comp}} \tag{2}$$

For the volume $V_{comp}=0.5l$ and overpressure of $P_{max}=1000$ Pa, estimated air flow $f_1$ is about 0.02 l/s. At this low air flow, pressure drop across airway resistance is negligibly small and alveolar pressure is close to mouth pressure.

Preferable duration of the occlusion can be about 0.3-1 s. For implementation of the proposed method, it may be advantageous to control the pressure versus time waveform and reject trials where $P_{max}$ was reached too fast, say faster than for 0.2 s. An appropriate message can be generated in this case to advise the subject to produce slower exhalation, or the measurement can simply be rejected.

Figure 3:
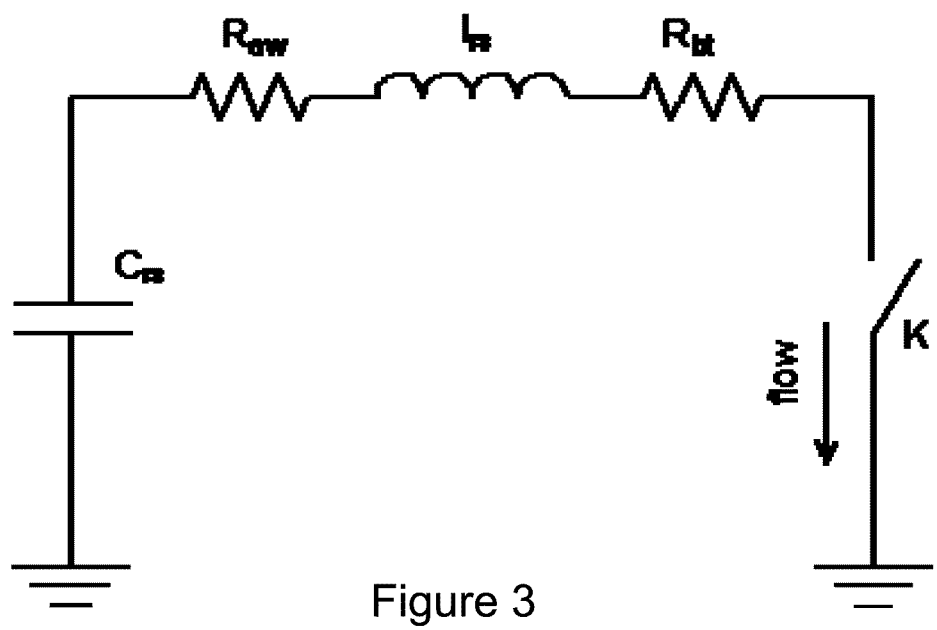
FIG. 3 shows simplified electrical model of the respiration system.

Representation of respiration system in terms of electrical components helps to build simple models for analysis of air flow waveforms. FIG. 3 illustrates a simplified electrical model of the respiration system. Here resistance $R_{aw}$ and inertance $I_{rs}$ are the sum of airways, lung tissue and chest wall contributions. Compliance $C_{rs}$ is determined mainly by lung tissue and chest wall compliances. Shutter 4 is presented schematically by switch K (initially opened). Compression of air inside the lung at the beginning of the testing procedure is equivalent to charging of the capacitance $C_{rs}$. Opening of the shutter 4 is equivalent to closing of the switch K.

Air flow f(t) through the breathing tube after opening of the shutter 4 can be found from the equation for the linear circuit:

$$I_{rs}\frac{d^2 f(t)}{dt^2} + (R_{aw}+R_{bt})\frac{df(t)}{dt} + \frac{1}{C_{rs}}f(t) = 0 \tag{3}$$

Equation (3) describes the discharge of the capacitance $C_{rs}$ through resistance $R_{aw}+R_{bt}$ and inductance $I_{rs}$.

To simplify the qualitative analysis of eqn. (3), assume that $R_{aw}$ and $R_{bt}$ do not depend on flow and $(R_{aw}+R_{bt})^2 \gg I_{rs}/C_{rs}$. Under these assumptions, the solution of eqn. (3) can be presented as:

$$f(t) \approx \frac{P_{max}}{R_{aw}+R_{bt}}\left[\exp\left(-\frac{t}{\tau_1}\right) - \exp\left(-\frac{t}{\tau_2}\right)\right], \tag{4a}$$

where $$\tau_1 = (R_{aw}+R_{bt})C_{rs} \tag{4b}$$

$$\tau_2 = \frac{I_{rs}}{R_{aw} + R_{bt}} \quad (4c)$$

Time $t_p$ equals:

$$t_p \approx \tau_2 \ln\frac{\tau_1}{\tau_2} \quad (5)$$

Substituting values for airway resistance, lung compliance and inertance $R_{aw}$=200 Pa*s/l, $C_{rs}$=10$^{-3}$ 1/Pa, $I_{rs}$=1 Pa*s$^2$/l and $R_{bt}$=50 Pa*s/l, obtain: $\tau_1$=250 ms, $\tau_2$=4 ms, $\tau_p$≈16 ms. The flow waveform f(t) is shown on FIG. 4 (opening pressure of the shutter is 1000 Pa).

Figure 4:
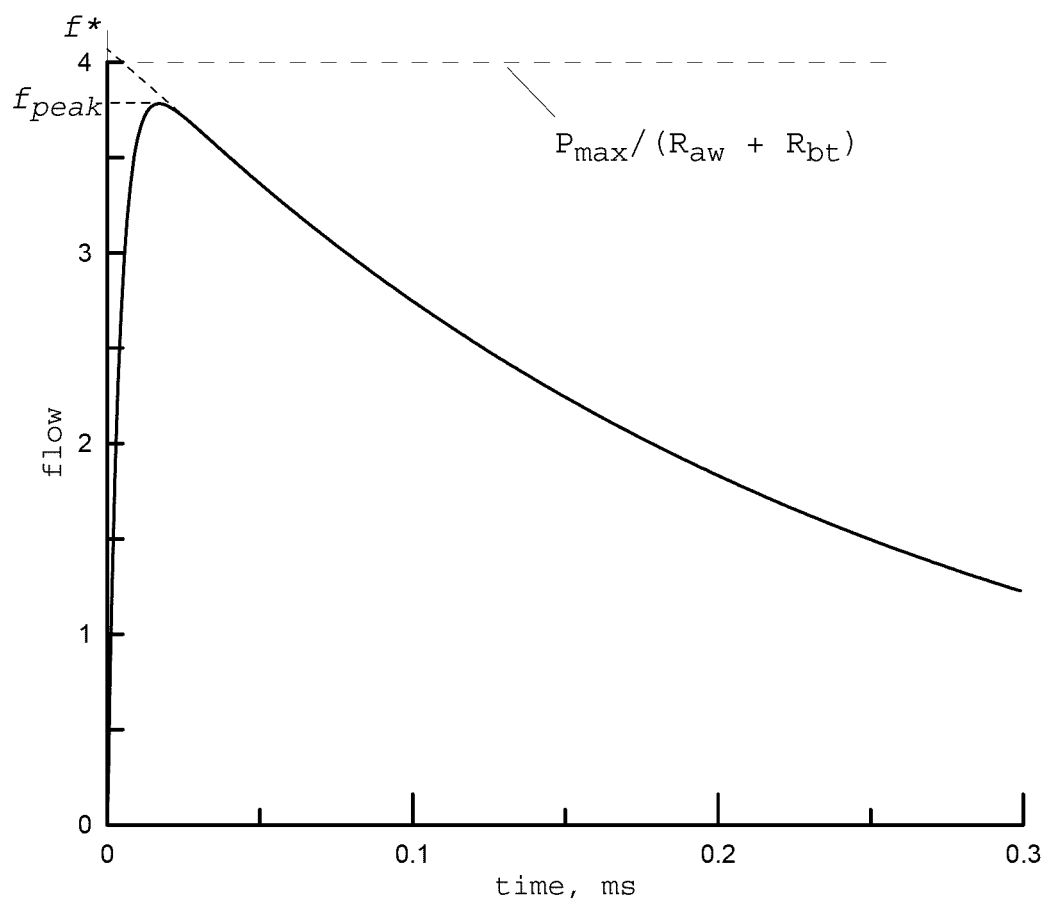
FIG. 4 shows calculated flow waveform after shutter opening.

In accordance with the proposed method, the value of the airway resistance is determined from the measured flow waveform f(t). In one possible procedure, the straight line tangent to the flow-time curve is built as shown in FIG. 4 and its interception f* with the flow axis is found. Airway resistance is determined as:

$$R_{aw} = \frac{P_{max}}{f^*} - R_{bt} \quad (6a)$$

A simpler way to determine $R_{aw}$ can be used based on the fact that usually $\tau_1 \gg \tau_2$ and peak flow $f_{peak}$ and flow f* are approximately the same. In this case:

$$R_{aw} = \frac{P_{max}}{f_{peak}} - R_{bt} \quad (6b)$$

Lung compliance $C_{rs}$ can be determined from the flow waveform generated after the shutter opening. The slope of the straight line shown in FIG. 4 and built after flow reached its peak (t$\gg\tau_2$), depends on compliance and can be estimated from:

$$\frac{1}{f(t)}\frac{df(t)}{dt} \approx -\frac{1}{(R_{aw}+R_{bt})C_{rs}} \quad (7a)$$

or $$\ln(f(t)) \approx -\frac{1}{(R_{aw}+R_{bt})C_{rs}}t + A, \quad (7b)$$

where A is an integration constant.

In accordance with some embodiments, the airway resistance $R_{aw}$ is determined first as described by eq. 6. Then lung compliance $C_{rs}$ can be determined from eq. 7.

Figure 5:
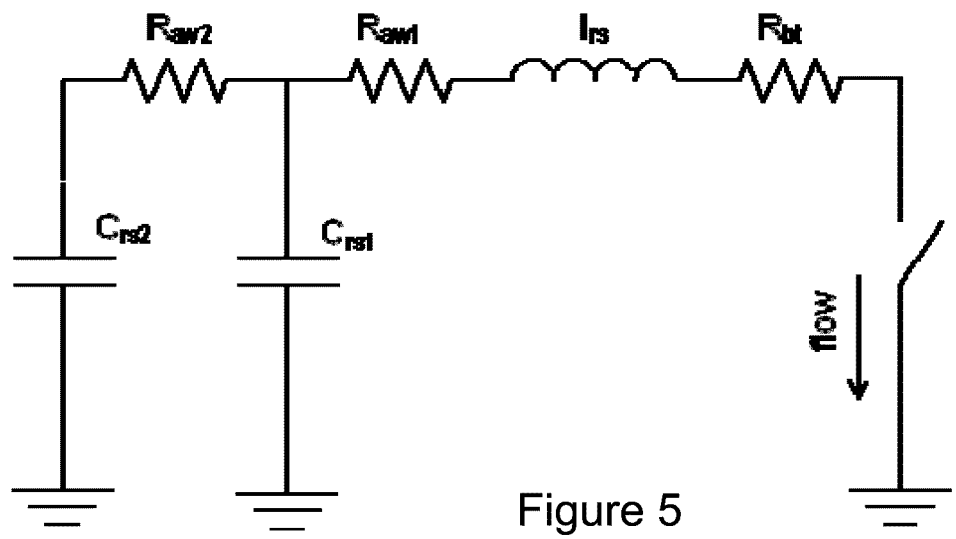
FIG. 5 shows electrical model of the respiration system where upper and lower levels of lung are represented with different R L C networks.

More advanced models of the human respiratory system [I. Jabłoński, A. G. Polak, J. Mroczka, "A Complex Mathematical Model of the Respiratory System as a Tool for the Metrological Analysis of the Interrupter Technique", XIX IMEKO World Congress Fundamental and Applied Metrology, Sep. 6-11, 2009, Lisbon, Portugal, pp. 1601-1604] represent the electrical equivalent of the respiratory tree as a ladder network consisting of the resistance-capacitance-inductance cells describing 24 generations of the airways. Understanding of the influence of the distribution of resistances across the bronchial tree corresponding to different levels of airways obstruction on the shape of flow waveform is important for evaluation of the respiratory system. Quantitative analysis without complex calculations was performed for a simplified network representing the respiratory system shown in FIG. 5.

Figure 6:
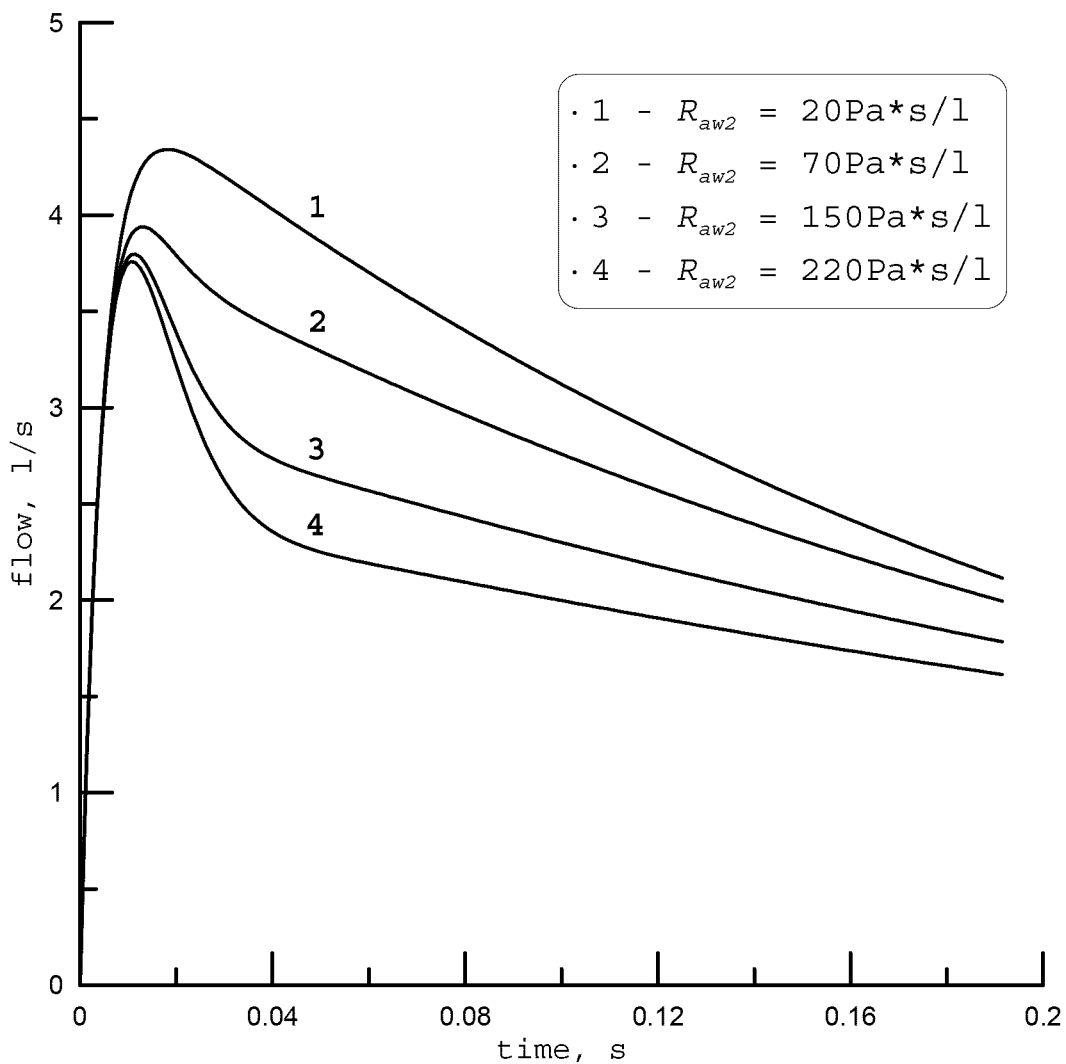
FIG. 6 shows flow waveform at different values of Raw2 representing resistance of small airways.

The network consists of two parts. One part represents upper airways and upper part of the central airways with assigned resistance $R_{aw1}$, compliance $C_{rs1}$ and inertance $I_{rs1}$. The second part represents the lower part of the central airways and peripheral airways with resistance $R_{aw2}$ and compliance $C_{rs2}$. The analysis was performed for the following assumptions: $R_{aw1}$=150 Pa*s/l, $C_{rs1}$=10$^{-4}$ 1/Pa, $C_{rs2}$=10$^{-3}$ 1/Pa, $I_{rs1}$=1 Pa*s$^2$/l, $R_{bt}$=50 Pa*s/l. The opening pressure of the shutter is 1000 Pa. FIG. 6 shows flow waveforms calculated at different values of $R_{aw2}$.

For the analysis of the flow waveform, it may be convenient to plot it in a way such that its fragments describing the exponential decrease of flow $$f(t) \sim e^{-\frac{t}{\tau}}$$

are represented by line segments with a slope determined by a time constant $\tau$. Assume that flow reduces in the interval between time $t_1$ and $t_2$ as:

$$f(t) = f_1 e^{-\frac{t-t_1}{\tau}}, \quad (8)$$

where $f_1$ is the flow at t=$t_1$ and $$\tau = \frac{1}{(R_{aw}+R_{bt})C_{rs}}$$

is a time constant. Taking the logarithm of eq.(8), we obtain:

$$\ln(f(t)) = \ln(f_1) + \frac{t_1}{\tau} - \frac{t}{\tau} \quad (9)$$

The logarithm of flow ln(f(t)) is a linear function of time in the interval $t_1$<t<$t_2$ with a slope inversely proportional to time constant r.

If the exhaled volume is calculated as the integral of flow over time since shutter opening, its value in the same interval $t_1$<t<$t_2$ equals:

$$Vol(t) = Vol_1 + \tau f_1\left(1 - e^{-\frac{t-t_1}{\tau}}\right) = Vol_1 + \tau f_1 - \tau f(t), \quad (10)$$

where $Vol_1$ is volume at t=$t_1$.

Eq.(10) can be transformed to:

$$f(t) = \frac{Vol_1}{\tau} + f_1 - \frac{1}{\tau}Vol(t) \quad (11)$$

The flow versus volume function is linear in the interval $t_1$<t<$t_2$ with a slope inversely proportional to time constant $\tau$.

Therefore, if the flow waveform is plotted with axes ln(flow)-time or flow-volume and contains fragments with different slopes, it can be interpreted that time constant τ varies with time or with exhaled volume.

Figure 7:
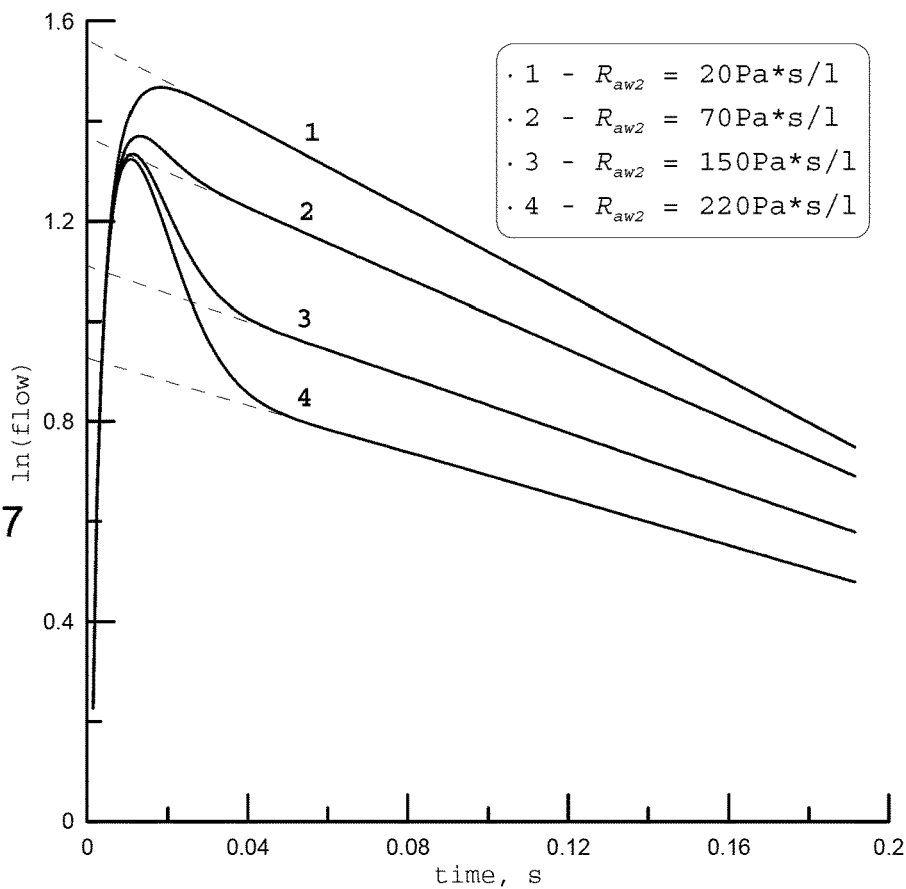
FIG. 7 shows calculated waveforms at different levels of Raw2 built in axes ln(flow)–time.
Figure 8:
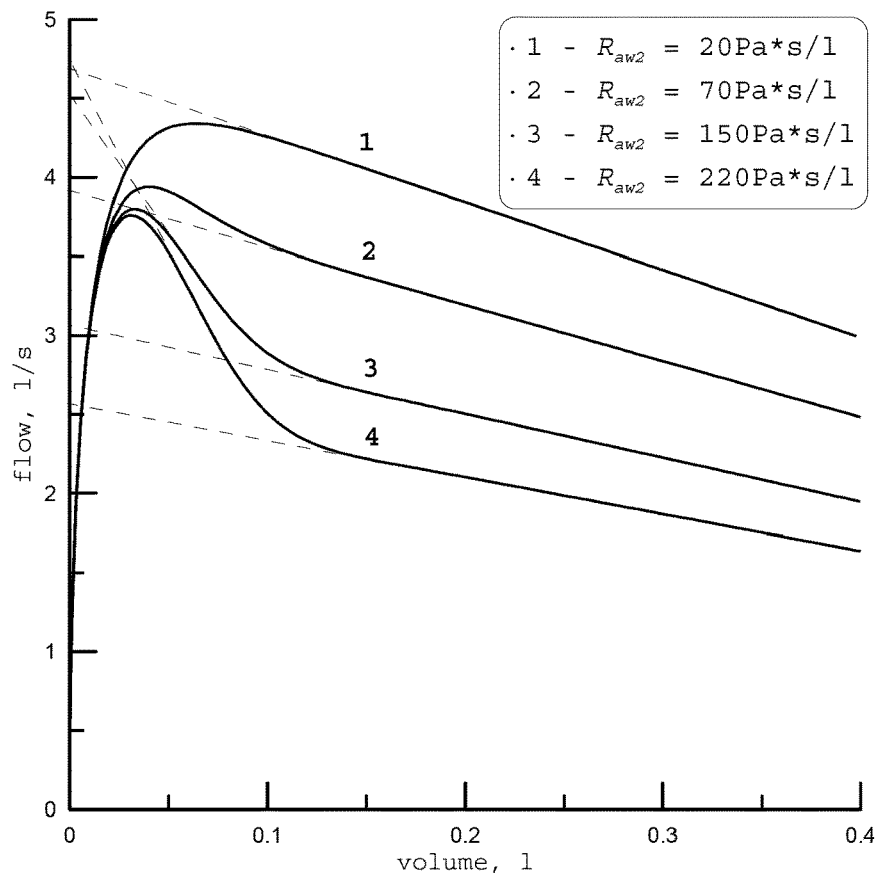
FIG. 8 shows calculated waveforms at different levels of Raw2 built in axes flow-volume.

FIGS. 7 and 8 present calculated flow waveforms plotted with axes ln(flow)-time and flow-volume. The increase of $R_{aw2}$, which corresponds to increasing obstruction of small airways, "bends" the flow curves down. The part of the waveform with steep flow reduction is followed by a fragment with comparatively constant slope. This shape of the waveform can be explained. Air flow shortly after the shutter opening is determined mainly by the capacitance $C_{rs1}$ discharging through the resistance $R_{aw1}$ with time constant $R_{aw1}C_{rs1} \approx 15$ ms. In approximately 50 ms after the shutter opening, the dominant contribution to the air flow is provided by the capacitance $C_{rs2}$ which has a slower discharge rate than $C_{rs1}$ in case of a significant value of $R_{aw2}$. Capacitance $C_{rs2}$ is discharged through total airway resistance $R_{aw}=R_{aw1}+R_{aw2}$.

In the case of the essential resistance value of $R_{aw2}$, the calculation of total airway resistance $R_{aw}=R_{aw1}+R_{aw2}$ using the peak value of flow (eq. (6b)) becomes inaccurate. More accurately, airway resistance can be calculated by eq. (6a) where a straight line used to find the intercept flow f* using a tangent to the fragment of flow waveform, where flow decrease is mainly defined by discharge of the capacitance $C_{rs2}$.

FIGS. 7 and 8 show straight line tangents to ln(flow)-time and flow-volume curves used to find the intercept flow f*. Results of calculation of airway resistance obtained from equations (6b)-$R_{aw\_peak}$ and (6a)-$R_{aw\_intercept}$ are presented in table 1.

TABLE 1

$R_{aw}$ calculation based on peak flow and interception flow.

| $R_{aw1} + R_{aw2}$, Pa*s/l | $R_{aw\_peak}$, Pa*s/l | $R_{aw\_intercept}$, Pa*s/l |
| --- | --- | --- |
| 170 | 181 | 163 |
| 220 | 203 | 207 |
| 300 | 213 | 278 |
| 370 | 217 | 341 |

Note that variation of resistance $R_{aw2}$ between 50 Pa*s/l and 220 Pa*s/l changes peak flow insignificantly—less than 7%. Meanwhile changes in the shape of flow waveform and more than 60% increase of $R_{aw\_intercept}$ can be used as more sensitive indicators of obstruction of small airways.

The rule for selecting the fragment of the flow-volume waveform to build the tangent line can be described as following. The slope of the waveform is zero at an extreme point where flow reaches its peak value then reaches a maximum absolute value and after that reduces to relatively constant level (FIG. 9). The fragment 16 is selected from the part of the waveform with a relatively constant slope. Interception of the straight line tangent to fragment 16 with the flow axis (i.e. at zero exhalation volume corresponding to the time of opening the shutter) gives the value of f*. After determining f*, the airway resistance can be calculated from eq.(6a) and then lung compliance—from the slope of this line segment 16 inversely proportional to the time constant τ.

The same approach can be used to define the fragment of the flow waveform for calculation of airway resistance and lung compliance from the flow waveform plotted with axes ln(flow)-time (FIG. 7).

The procedure for determining flow f* by finding the interception of the tangent line with the flow axis can be generalized. The flow f* can be determined for each point of the waveform and an appropriate value of airway resistance can be calculated from eq.(6a). FIG. 10 shows the calculated $R_{aw}$ as function of exhaled volume for three curves with modeled resistance $R_{aw2}$ of 70, 150 and 220 Pa*s/l (curves 2, 3, 4 on FIG. 8). Minimal resistance is obtained for the fragments with the steepest slopes of the waveforms which correspond to discharge of the capacity $C_{rs1}$ and equivalent to $R_{aw1}$. Lines tangent to the curves 3 and 4 at these points of the steepest slope intercept the flow axis at ~4.5l/c (see FIG. 8) which determines the $R_{aw}$ value close to $R_{aw1}$.

The difference between maximum (total $R_{aw}$) and minimal ($R_{aw1}$) resistance is resistance $R_{aw2}$ representing small airways (shown on FIG. 10). Therefore, the proposed method allows evaluation of not only total airway resistance but also its parts related to upper, central and small airways.

To implement the described method, the device comprising the shutter attached to the flowmeter can be used as shown in FIG. 1. The flowmeter can be either a standard one which is used in one of typical pulmonary function tests or a special one designed specifically for given application. The flowmeter preferably provides accurate measurement in the flow range of approximately 0.2 l/s to about 10 l/s, with a maximum flow rate measurement of about 6 l/s being often sufficient to directly measure the peak flow. The technique of measuring the slope of the flow curve to measure f* as described above can be used with a flow meter that fails to measure what is actually the full peak flow rate, as long as it can measure the lower flow levels of the curve immediately following the peak so as to determine the tangent of the curve and find accurately f*.

Figure 11:
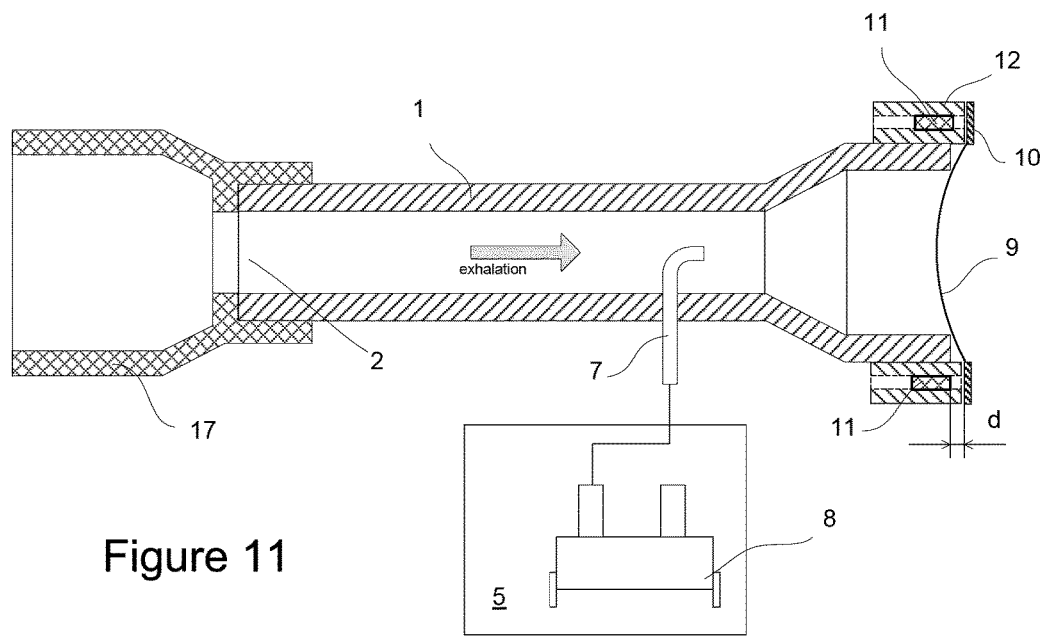
FIG. 11 is sketch drawing of the experimental respiratory device.

FIG. 11 illustrates a cross section of one possible embodiment of the proposed device. The experimental device comprises the flow tube 1 with the length of 100 mm and inner diameter of 15 mm at the center and 22 mm at the distal end. Metal or plastic tubing with inner diameter of 1 mm bent at its end and positioned inside the flow tube 1 as shown on the FIG. 11 is used as pressure probe 7.

The shutter contains light rigid plastic cap 9 with spherical surface and thin ferromagnetic metal ring 10 attached at its perimeter. The metal ring is attracted to the flow tube 1 by several miniature permanent magnets 11 fixed in a ring 12 attached at the end of the flow tube 1.

Opening of the shutter occurs when the pneumatic force which is equal to the product of air pressure inside the flow tube 1 and the area of tube aperture at its distal end exceeds the attraction force generated by the permanent magnets. The attraction force and hence air pressure needed to open the shutter are regulated by the number of magnets 11 and distance d between the magnets 11 and the metal ring 10. Note that the pressure needed to open the shutter depends also on the diameter of the tube aperture.

As described above, a manual release mechanism for the shutter or cap can be provided instead of an electrically controlled release.

One gauge sensor 8 is used to measure a) mouth pressure during occlusion when air is being compressed inside the closed tube and b) the pressure induced by air flow after opening of the shutter. During occlusion, the sensor 8 measures positive pressure which is fed to the sensor input through the pressure probe 7. As shown in FIG. 11, the sensor 8 has one port connected to the tube 7 and another port communicating with the ambient. After opening of the shutter, the sensor 8 measures negative pressure induced by gas flow passing through the tube 1.

The device contains a plastic mouthpiece 17 attached to the proximal end 2 of the flow tube 1. The mouthpiece can be of a variety to types. For example, it can be a small tube that the mouth fits over like in the case of a straw (fitting the lips around the tube) that can be the end of the tube 1 itself or a separate member, it can be a larger mouthpiece that is used like the mouthpiece of a trumpet (pressing the lips against the mouthpiece), or it can be a mouthpiece similar to a snorkel mouthpiece that the patient places in the mouth and can even bite for securing.

A snorkel type mouthpiece is secured with a flange between the gums and the lips of the subject. In this case, inserting the mouthpiece is more time consuming and it can be practical to breathe in with the mouthpiece in position. This can be done by leaving the shutter open for inhalation, and then closing the shutter for operation as described above, or an inlet can be provided. For example, an inhalation flap or check valve can be provided to allow the subject to breathe in. In one possible embodiment, this check valve can be provided within the shutter itself. This can allow for quiet breathing by the subject to begin with inhalation instead of exhalation.

As shown in FIG. 11, the mouthpiece 17 can be a replaceable and separable part from the tube 1. The tube 1 can be made so as to be sterilizable.

Figure 12B:
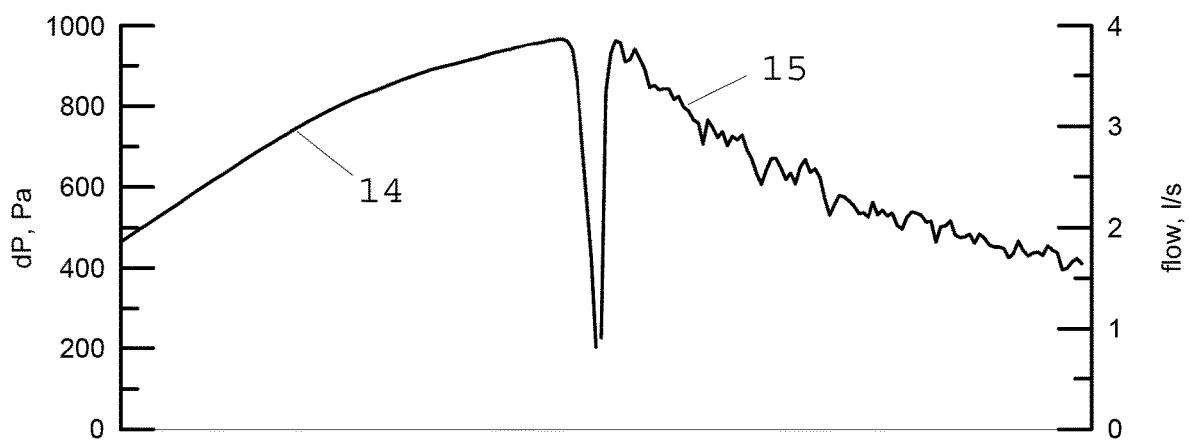
FIG. 12B presents derived mouth pressure and flow waveforms.
Figure 12A:
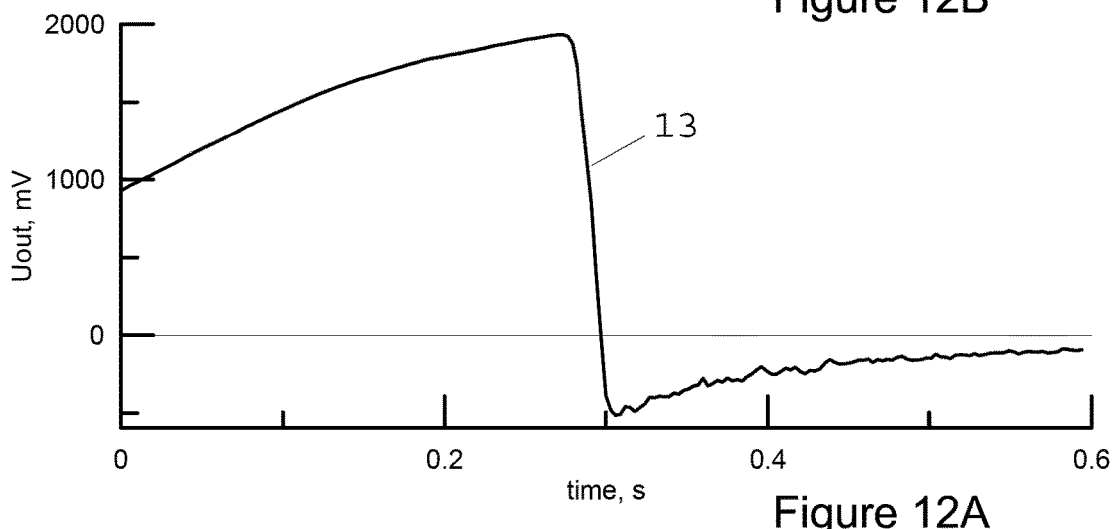
FIG. 12A presents typical voltage output during the test.

FIG. 12A shows the typical voltage response $U_{out}(t)$ 13 generated by the device at the exhalation of normal subject. The sensor 8 has a pressure sensitivity of 2 mV/Pa and a time response of 2 ms. The flow tube 1 with the pressure probe 7 and opened shutter generates pressure differential as function of flow approximated by formula:

$$dP = P - P_{atm} = -a * f^2 \quad (8)$$

where $a = 17.4$ Pa/(l/s)$^2$. Pneumatic impedance of the flow tube in the range from 1 l/s to 5 l/s is approximated as:

$$R_{bt} = 4.6 + 15 * f, \quad (9)$$

where $R_{bt}$ is measured in Pa*s/l and flow f is measured in l/s.

With this calibration data, mouth pressure and air flow produced after the shutter opening can be derived from the waveform 13. FIG. 12B presents mouth pressure 14 and air flow 15.

The measured time interval between the events of maximum mouth pressure and zero pressure is approximately 50 ms. Peak flow is reached in approximately 25 ms after the zero pressure event.

To evaluate the proposed method and verify functionality of the experimental device, several tests were performed. In the first test, the possibility to measure airway resistance changes emulated by external flow restrictors was checked.

Two external flow restrictors were built from a mesh of narrow plastic strips fixed inside a silicone tube with an inner diameter of 1.8 cm and length of 2.5 cm. The restrictor was plugged into the mouthpiece 17. The pneumatic resistance of the restrictor was determined as a ratio of back pressure and air flow through the restrictor. Both restrictors had resistance proportional to flow. Resistance of the first restrictor varied from 40 Pa*s/l to 60 Pa*s/l at flow from 2 l/s to 3 l/s. The second restrictor had a resistance between 70 Pa*s/l and 105 Pa*s/l in the same flow range.

Figure 13A:
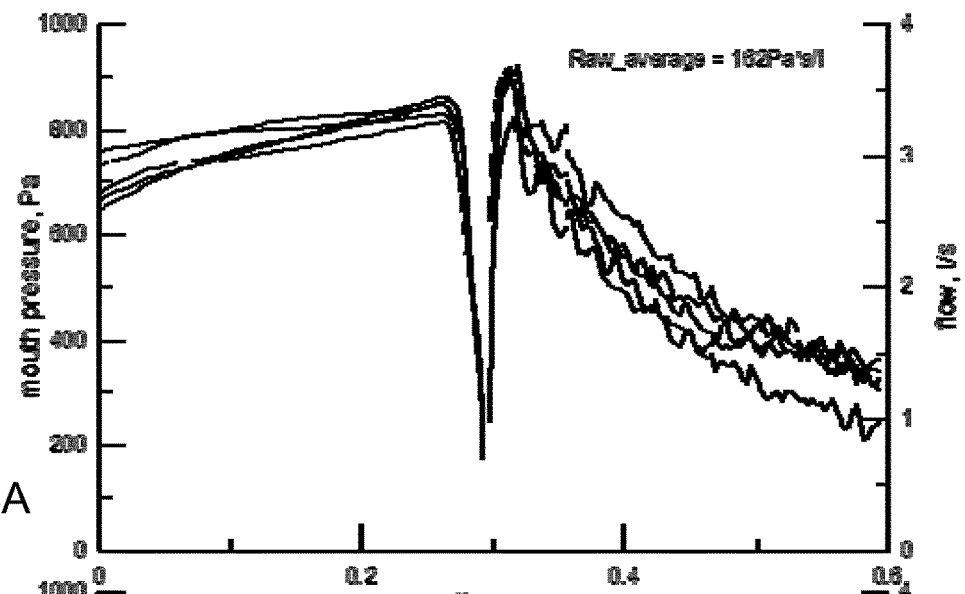
FIG. 13A presents mouth pressure and flow waveforms measured for a trial without external flow restrictors.
Figure 13B:
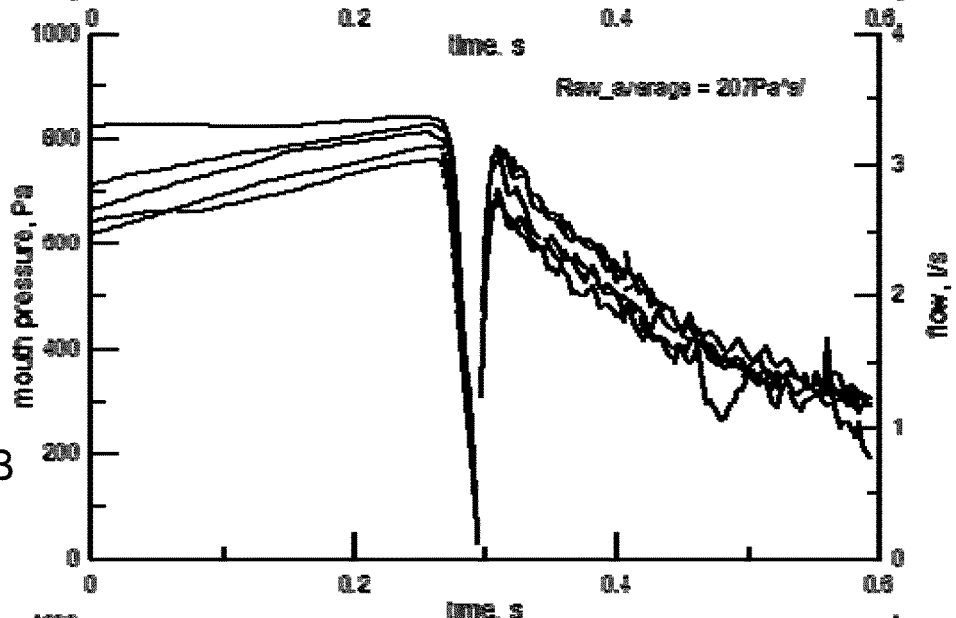
FIG. 13B presents mouth pressure and flow waveforms measured for a trial with external flow restrictor 1.
Figure 13C:
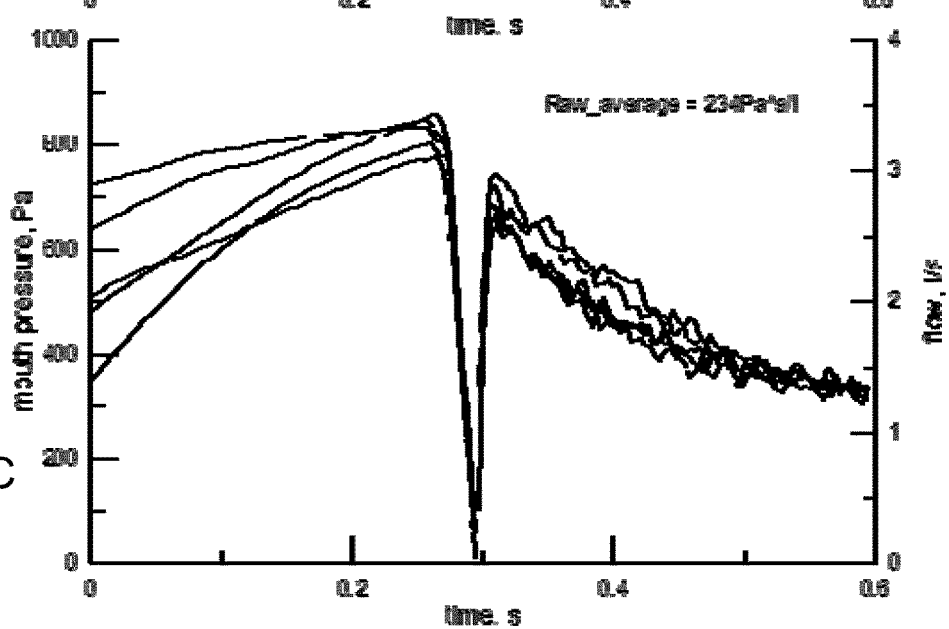
FIG. 13C presents mouth pressure and flow waveforms measured for a trial with external flow restrictor 2.

FIG. 13 shows pressure and flow waveforms generated by a normal subject without restrictor (FIG. 13A), with restrictor 1 (FIG. 13B) and restrictor 2 (FIG. 13C). Results of the measurements are presented in tables 2-4. Airway resistance was calculated in accordance with eq. (6b) based on peak flow value.

TABLE 2

$R_{aw}$ measurements without flow restrictors.

|  | trial 1 | trial 2 | trial 3 | trial 4 | trial 5 |
|---|---|---|---|---|---|
| $R_{aw}$, Pa*s/l | 156 | 161 | 177 | 158 | 157 |
| Average $R_{aw}$, Pa*s/l |  |  | 162 |  |  |
| Deviation from average $R_{aw}$, % | −3.6 | −0.7 | 9.8 | −2.4 | −3.1 |

TABLE 3

$R_{aw}$ measurements with flow restrictor 1.

|  | trial 1 | trial 2 | trial 3 | trial 4 | trial 5 |
|---|---|---|---|---|---|
| $R_{aw}$, Pa*s/l | 205 | 217 | 218 | 202 | 191 |
| Average $R_{aw}$, Pa*s/l |  |  | 207 |  |  |
| Deviation from average $R_{aw}$, % | −0.6 | 4.9 | 5.4 | −2.1 | −7.5 |

TABLE 4

$R_{aw}$ measurements with flow restrictor 2.

|  | trial 1 | trial 2 | trial 3 | trial 4 | trial 5 |
|---|---|---|---|---|---|
| $R_{aw}$, Pa*s/l | 225 | 227 | 232 | 237 | 249 |
| Average $R_{aw}$, Pa*s/l |  |  | 234 |  |  |
| Deviation from average $R_{aw}$, % | −4.0 | −3.1 | −0.7 | 1.3 | 6.5 |

TABLE 5

End-of-test $R_{aw}$ measurements.

|  | trial 1 | trial 2 |
|---|---|---|
| $R_{aw}$, Pa*s/l | 160 | 159 |
| Average $R_{aw}$, Pa*s/l |  | 159 |
| Deviation from average $R_{aw}$, % | 0.34 | −0.34 |

Each measurement was performed five times at an interval of ~1 minute between trials. At the end of the test, two control trials were done without restrictors to check if any changes of airway resistance were caused by multiple measurements. Results of two last trials are presented in table 5.

An increase of average airway resistance of 45 Pa*s/l and 72 Pa*s/l was detected for the tests with flow restrictors 1 and 2 that corresponds reasonably to their pre-measured pneumatic resistances. Multiple measurements of $R_{aw}$ which require just quiet single exhalation through the flow tube are not serious exercise for the subject and do not change value of $R_{aw}$ that was confirmed by the end-of-test measurements.

Lung compliance was also calculated during the test in accordance with eq. (7). Its averaged value was determined to be $0.93*10^{-3}$ l/Pa (no restrictors), $1.005*10^{-3}$ l/Pa (restrictor 1) and $0.935*10^{-3}$ l/Pa (restrictor 2). As expected, no significant changes in lung compliance were detected. Repeatability of lung compliance measurements of about 20% was worse than repeatability of $R_{aw}$ measurements.

Figure 14:
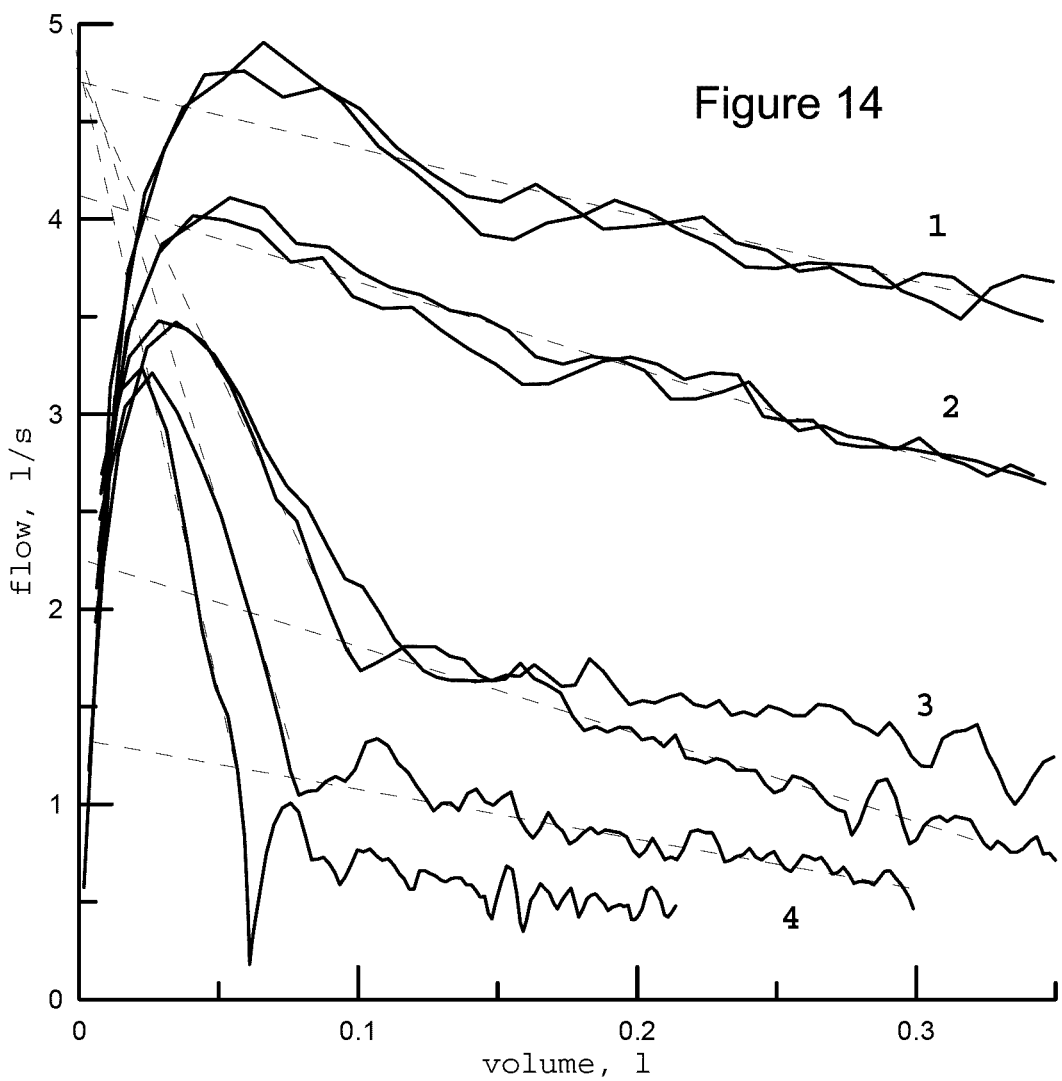
FIG. 14 shows flow-volume waveforms generated by the subject at different levels of lung volume.

A second test was performed to check the ability of the device to measure real "physiological" changes in airway resistance. The tests were done at different volumes of respiratory system—close to 100% of total lung capacity (TLC), after inspiration during quiet breathing, and near residual volume (RV). The first test was performed after maximum inhalation. In the third case, the subject performed test after deep and "very deep" (almost maximum) exhalation. FIG. 14 shows flow-volume curves measured in several trials at different levels of lung volume.

As expected, the extension of the lung accompanied with a widening of the airways reduces airway resistance. Trials done after deep exhalation demonstrate also significant obstruction of small airways resulting in "bending" of the flow-volume curves. While the difference in peak flows between trials 2, 3 and 4 is not significant, interception flow for trials 3 and 4 is essentially reduced that determines much higher total airway resistance.

Note that lines tangent to the curves 2, 3, 4 at their steepest portions intercept with the flow axis at approximately the same zone of 4.5-5 l/s that defines almost the same resistance of upper airways for these tests. $R_{aw2}$ and total airway resistance are essentially different for these trials.

Figure 15:
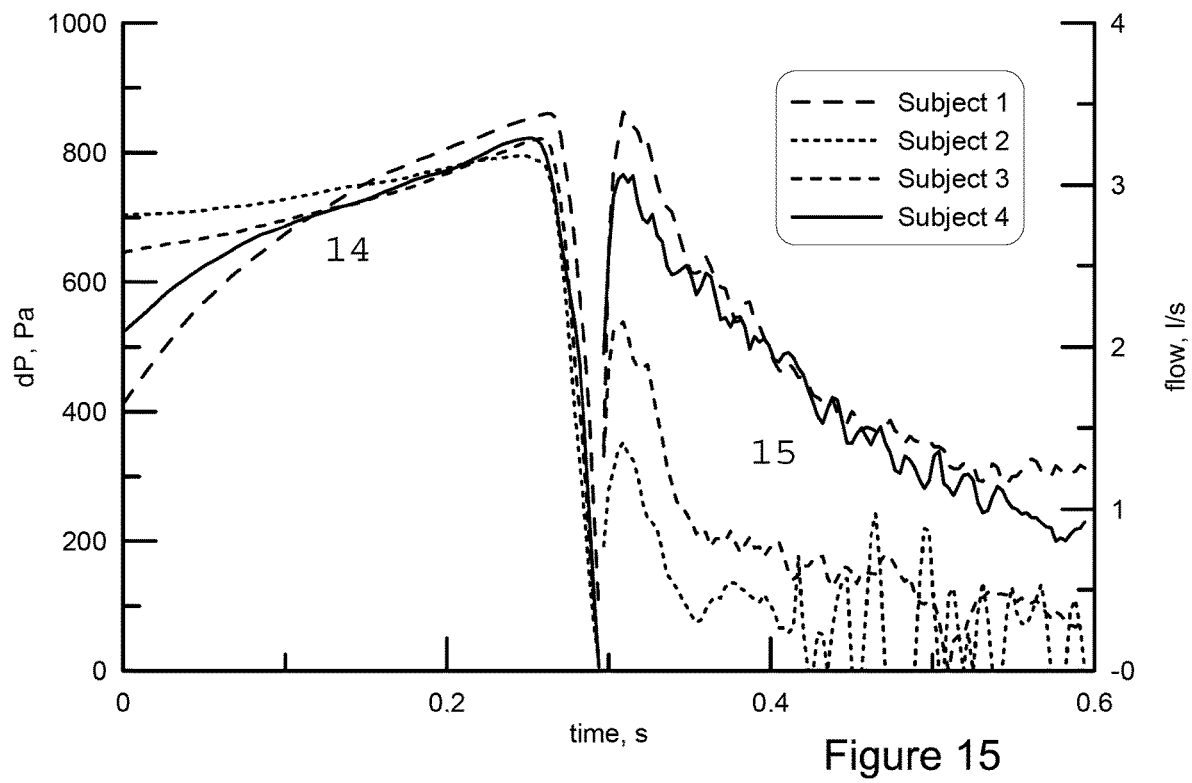
FIG. 15 shows experimental mouth pressure and flow waveforms measured for four different subjects.

FIG. 15 shows pressure and flow waveforms measured for four different subjects with different levels of airways resistance. The threshold opening pressure of the shutter was adjusted to approximately 800 Pa for this test. Peak flow for subjects 1 and 4 exceeded 3 l/s and was significantly higher than typical flow at quiet exhalation. The peak flow for subject 3 with higher airway resistance reached a peak value of 2.2 l/s which is still essentially higher than flow at quiet exhalation.

High airway resistance of subject 2 was the reason why peak flow was limited to 1.4 l/s. To increase peak flow and make more accurate measurements for the subjects with high airway resistance such as patients with serious obstructive diseases and preschool children, it may be advantageous to increase opening pressure of the shutter. The actual value of the opening pressure should be chosen so as not to create excessive inconvenience for the subject and from the other side, to reach peak flow at the level of 2-3 l/s or higher clearly distinguishable over a background of quiet exhalation.

One of the possible rules to set opening pressure $P_{max}$ may be the following combination of conditions:

$P_{max}$=900 Pa for subjects with airway resistance $R_{aw}$<300 Pa*s/l;
$P_{max}$=(3 l/s)*$R_{aw}$ for 300 Pa*s/l $R_{aw}$<500 Pa*s/l;
$P_{max}$=1500 Pa for 500 Pa*s/l<$R_{aw}$<750 Pa*s/l;
$P_{max}$=(2 l/s)*$R_{aw}$ for $R_{aw}$<750 Pa*s/l;
the maximum value of $P_{max}$ is limited by 2000 Pa.

Another possible rule to trigger the shutter can be to look for stabilization in the pressure build up as shown in FIG. 2. This can involve, for example, detecting a first slope threshold corresponding to a normal pressure rise indicative of relaxation and quiet exhalation, followed by a drop in the slope of the pressure curve to a second threshold. Once this condition is detected, opening of the shutter can be done immediately or shortly thereafter.

Another possible rule to trigger the shutter can be to detect that a first pressure threshold, for example 300 Pa, is exceeded for a predetermined time period, such as 250 ms—a time normally sufficient to reach pressure stabilization, without exceeding a second pressure threshold indicative of forced exhalation, such as 800 Pa for a child and 1600 Pa for an adult.

Concerning the described embodiment, such adjustment of opening pressure of the shutter can be reached by regulation of attraction force created by permanent magnets 11. To change attraction force, it is possible to change number of magnets, gap between magnets and metal ring 10 or change magnetic strength of the magnets. For more advanced devices with electromagnets, $P_{max}$ can be regulated automatically by using readings of pressure sensor to switch the magnets off at appropriate time during occlusion.

As was described above, the maximum lung pressure after occlusion should not exceed essentially the shutter opening pressure. In other words, the subject should not apply efforts to force his/her exhalation after the shutter is opened. It also should be understood that if shutter opening pressure is set too low, i.e. significantly lower than intra-lung pressure which would be created in case of spontaneous exhalation, this condition may not be reached and breathing pressure after shutter opening will exceed shutter opening pressure significantly. Therefore it may be advantageous to use an adaptive shutter opening algorithm based on an analysis of pressure inside the flow tube and the rate of pressure change. For example, pressure must exceed a predetermined level which may be set for the subjects of different age groups and/or expected level of airway obstruction. In addition to this condition, it may be advantageous also to control the rate of pressure increase during occlusion and to initiate shutter opening after the rate is lower than a predetermined level. Reduction in the rate of pressure increase during occlusion may be an indicator that lung pressure is approaching its maximum value that can be created by the subject during spontaneous exhalation. If the shutter is opened at this moment, a further increase of lung pressure is hardly possible (if the subject does not apply extra efforts intentionally) due to rapid air deflation from lung.

Figure 16A:
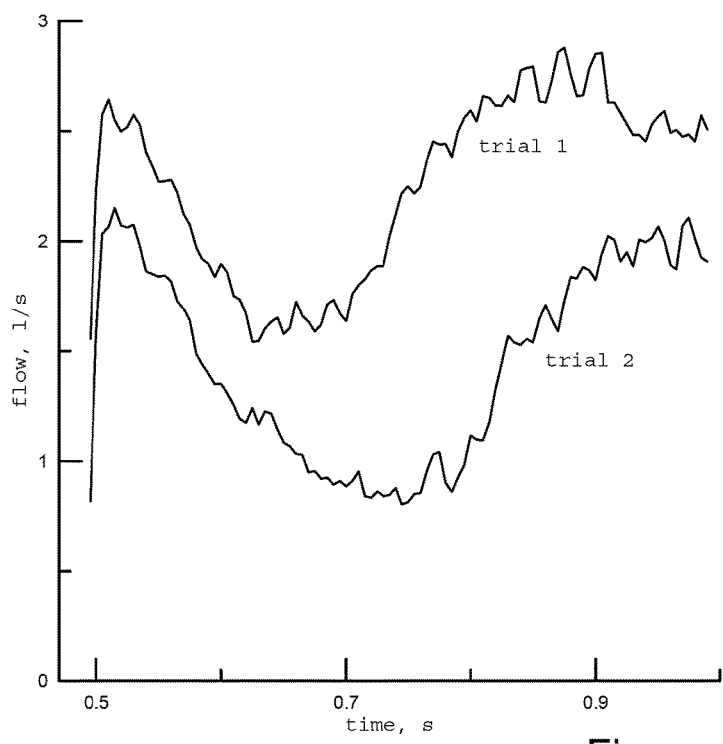
FIG. 16A shows flow waveforms for different trials performed by the subject with applying extra efforts during exhalation.
Figure 16B:
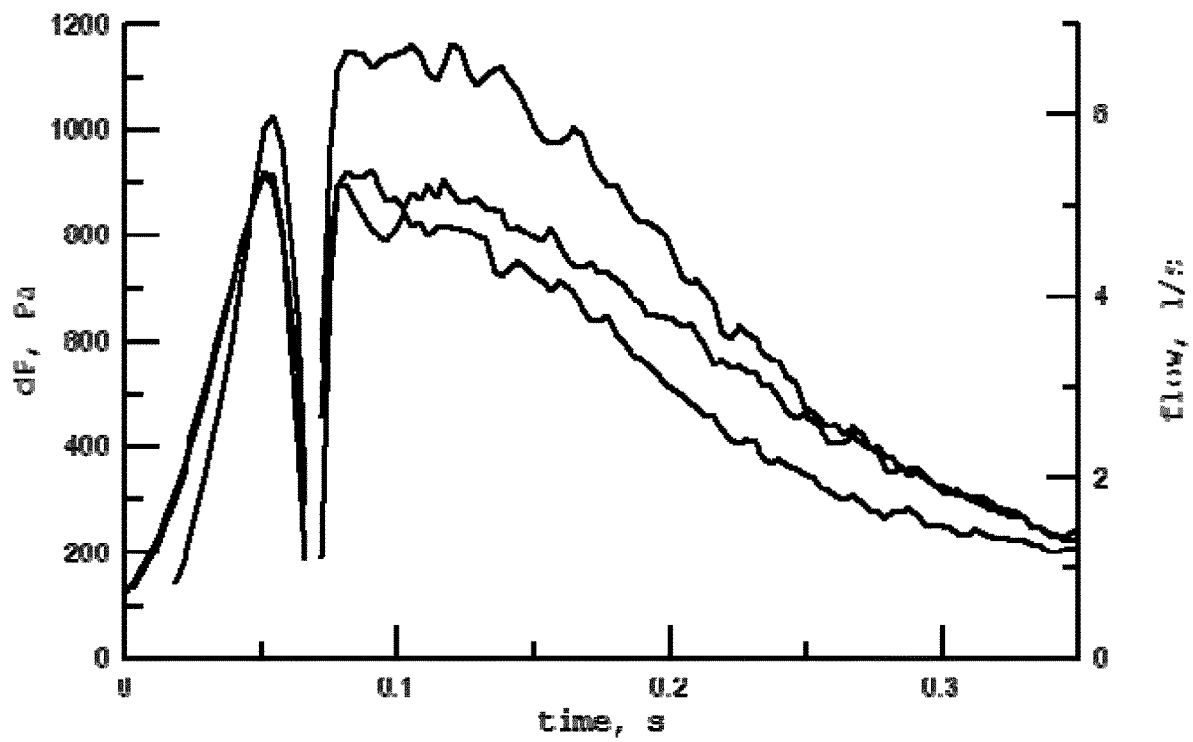
FIG. 16B shows flow waveforms for different "wrong" trials performed by the subject with applying extra efforts during exhalation.

It should be understood that attempt of the subject to produce forced exhalation violates the method and corrupts measurement data. FIG. 16A and 16B illustrates possible types of corruption caused by wrong exhalation. FIG. 16A shows one normal trial (dashed line) and two "wrong" trials produced by the same subject who intentionally tried to exhale faster during occlusion and accelerate exhalation after occlusion. Peak flow caused by the opening of the shutter is almost the same for all three trials but the shape of flow spike waveforms is essentially different due to imposing of flow expired too fast. Peak flow of the spike can provide almost correct data for calculation of airway resistance but attempts to determine lung parameters from the spike waveform (150-200 ms after peak) will give obviously wrong results.

FIG. 16B shows three "wrong" trials produced by the same subject who intentionally started to exhale fast from the early beginning of the test. Forced exhalation resulted in short occlusion of about 0.1 s and peak flow of 5-6 l/s which is significantly higher than peak flow measured at normal trial. Data from these trials cannot be used for calculation of lung parameters as was discussed above.

It may be advantageous for the proposed device to implement trial selection algorithm to identify trials performed wrong with applying of unnecessary forced efforts during exhalation. Such trials should be rejected and warning message can be generated to provide guidance for the subject.

Figure 17:
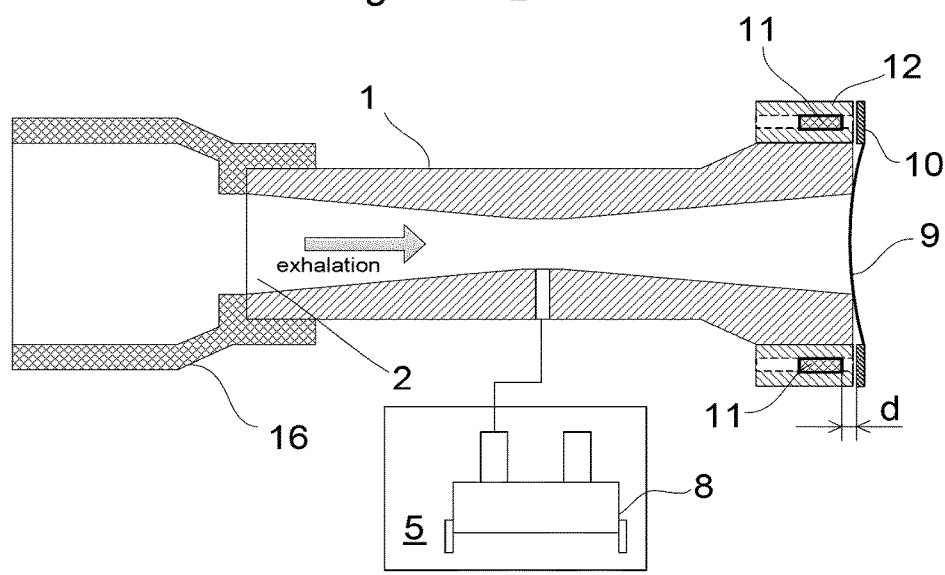
FIG. 17 is sketch drawing of the respiratory device based on Venturi tube.

FIG. 17 shows another possible embodiment of the respiratory device. Flow-to-pressure element of the device is based on a Venturi tube. Operation of the device is analogous to those of the first embodiment described above. Gauge sensor 8 measures a positive pressure differential relative to ambient pressure during the occlusion stage and then a negative pressure differential when air flow passes though Venturi tube after the shutter opening.

It may be advantageous to use a thermal micro-flow sensor of calorimetric type as gauge sensor 8, such as the LBA series from Sensortechnics Corp., or the AWM series from Honeywell, Inc., that are packaged to have two ports, the flow through which is measured. The sensors of this type have wide dynamic range and operate from about 2 kPa down to fraction of Pa. This performance is important for measuring of mouth pressure which may reach level of 1-2 kPa. At the same time the sensors provide low noise and high resolution at low differential pressure which is important for flow measurements with the use of Venturi, Pitot tubes or flow-to-pressure converters of other types.

It is known that sensitivity of the calorimetric type sensors is proportional to atmospheric pressure that typically requires additional sensitivity correction due to the variation of atmospheric pressure. A useful feature of the proposed design based on a thermal micro-flow sensor for measuring of both mouth pressure and flow is that atmospheric pressure correction is not needed for airway resistance measurement. Such a simplification of the device is possible because though both separate measurements of mouth pressure and flow are affected by ambient pressure, airway resistance which depends on their ratio stays unaffected by changes of atmospheric pressure.

Previous considerations are applied in general to sensitivity variation of pressure sensor caused by other factors like temperature drift or long-term instability. If two measurements are done by one sensor and airway resistance is determined by their ratio then final result is unaffected by possible sensitivity variations. Note that usage of two different sensors for each of these measurements may result in total inaccuracy because their sensitivities may drift differently.

As was described in one embodiment above, the shutter opening pressure can be set to a certain level with permanent magnets by adjusting their position in the shutter module and changing their number and/or magnetic strength. If opening of the shutter should be initiated adaptively when certain conditions for pressure and pressure increase rate are reached during occlusion, the attraction force near the location of at least one magnet can be intentionally reduced for a short period of time sufficient for the shutter opening, by moving of at least one of the permanent magnets from the metal ring or by use of additional electromagnets which counteracts the permanent magnet.

The described embodiment illustrates main guidelines for building of the device used for implementation of the proposed method. Design of the flow tube combined with pressure sensor can be simplified such that just one gauge sensor can be used to measure both mouth pressure and air flow. There is no need to measure air flow accurately below ~0.2 l/s, and pressure sensor with measurement range of ~2 kPa and resolution of better than 0.5-1 Pa can be acceptable for this application.

It should be noted that additional technical solutions may be used by those skilled in the art to improve and extend some features of the device. For example more advanced shutter can be used to provide faster opening or more accurate control of the opening pressure. It is also possible to synchronize shutter opening and closing with breathing cycles to perform measurements continuously during quiet breathing.

The design of the functional element generating negative pressure at flow through the tube can be also different from the design described in the embodiment.

It is possible to use existing flowmeter which is used for one of the standard pulmonary function tests to implement the method. In this case, a shutter with pressure sensor for mouth pressure measuring should be attached to the flow tube. In general devices implementing traditional interruption technique also can be used if their flowmeter is fast enough to measure accurately flow spike after shutter opening, and sequence of flow and pressure measurements is changed in accordance with disclosed method.

Figure 18:
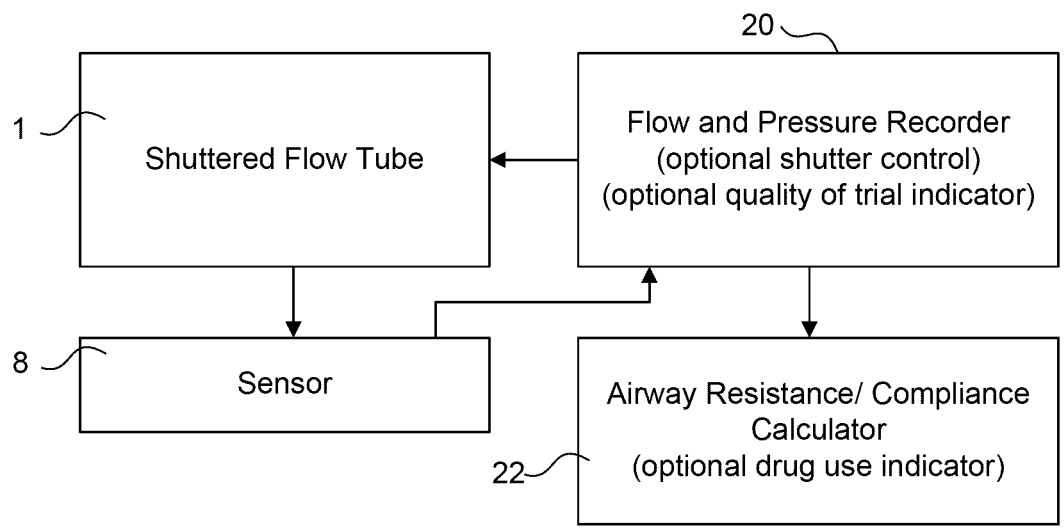
FIG. 18 is a schematic block diagram of the measurement device and signal processing system.

FIG. 18 shows a block diagram of the measurement device. As illustrated, the sensor 8, for example as described above in reference to the embodiments of FIGS. 1, 11 and 17, measures pressure and flow in the tube 1. A microcontroller, or other suitable circuitry, can be provided to control the recording of data in memory. This is schematically illustrated as a flow and pressure recorder 20. This unit 20 can also be responsible for controlling the shutter in the case that the shutter is automatically released. This unit 20 can also monitor the pressure and flow signals and determine if a measurement trial has the correct characteristics to produce good data, and provide an indicator, for example an audio signal or beep, when a trial was good and/or when a trial was not good and should be repeated. For example, if forced exhalation is detected, then the trial should be repeated.

A calculator for calculating airway resistance and/or compliance in accordance, for example following the methods and equations described above, is schematically illustrated as unit 22 in FIG. 18. It will be understood that this module can be provided in software in suitable microcontroller or other data processor.

The unit 22 can optionally indicate to the subject if the values calculated suggest a need or lack of need for a therapeutic or symptom control drug. Such calculations for determining a need or lack of need for use of a drug can use historical data of past measurements for the patient, and optionally external data such as local weather or pollution in the case of asthma control.

The units 20 and/or 22 can also be wirelessly coupled, for example using a Bluetooth interface, to the flow tube 1 and sensor 8. In this case, a handheld computer, such as a smart phone, tablet computer or dedicated device, can receive pressure and flow data from sensor 8 and perform storage and calculations using the computer. By using app software in the handheld, the patient can have access to a rich interaction with the data and the related analysis thereof. Current measurements can be compared with historical data to give an indication of improvement or worsening of condition. The trial data can also then be shared from the locally coupled computer with a healthcare professional, for example over the Internet, to obtain advice about the current condition.

In one embodiment, the device 1,8 has an electronic controller with a memory 20 for storing pressure and flow data from trials. The controller also includes an audio output and/or visual signal output to signal to the user whether a trial was good or needs to be repeated. The device can have its own battery and be easily portable. The device can also be self-sufficient to record trials without the use of the computer device that is used to display data, or to interact with the patient or healthcare professionals. Optionally the device can have a USB or other wired connector to transfer trial data from memory 20 to a computer where further analysis or calculations can be done. The device can be charged using such a wired connector.

The trial data in the device can be encrypted. The software used in the computer that analyses the trial data can decrypt the trial data. Use of the device can also be controlled such that the device can only be used with predetermined software and/or with a predetermined subscription for authorized usage. By allowing such control over how the device's data is used and processed, it is possible to ensure better quality of patient data handling and patient interaction. It is also possible to reduce the initial cost of purchasing the device if subscription revenue is expected to follow as the device is used over time.

The invention claimed is:

1. A method of measuring of at least one of airway resistance and lung compliance using a device comprising a flowmeter measuring pressure and flow, a releasable shutter and a processor associated with the flowmeter and said releasable shutter, said flowmeter initially closed by said shutter and comprising an occlusion stage when air inside a lung and the flowmeter is compressed until build-up pressure reaches a predetermined shutter opening threshold and stage of exit of the compressed air through the opened flowmeter, the method comprising:
   instructing a subject to perform quiet inhalation followed by quiet exhalation into said flowmeter;
   occluding a distal end of said flowmeter at a beginning of said quiet exhalation to provide air compression in said flowmeter;
   said device detecting air pressure during said occluding;
   said device removing occlusion of said distal end of said flowmeter in response to said detecting to create a post-occlusion flow spike having a post-peak duration less than about 200 ms;
   said device measuring flow in said flowmeter to obtain data representing said post-occlusion flow spike specifically during time interval less than said about 200 ms;
   said subject continues said quiet exhalation through said flowmeter after said removing occlusion of said distal end of said flowmeter; and
   determining said at least one of airway resistance and lung compliance from said post-occlusion flow spike data between a peak flow value and up to less than 200 ms following said peak flow values and air pressure inside the flowmeter measured before said shutter opening.

2. The method of claim 1 wherein said air compression during said occlusion stage is performed longer than 0.2 seconds.

3. The method of claim 1 wherein said airway resistance represents resistance for upper airways and an upper part of central airways $R_{aw1}$ is determined from maximum air pressure $P_{max}$ measured before said shutter opening and peak flow $f_{peak}$: $R_{aw1} = P_{max}/f_{peak} - R_{bt}$, where $R_{bt}$ is pneumatic impedance of the flowmeter.

4. The method of claim 1 wherein said airway resistance represents resistance for a total of upper airways and lower airways $R_{aw}$ is determined from maximum air pressure $P_{max}$ measured before said shutter opening and flow value $f^*$: $R_{aw} = P_{max}/f^* - R_{bt}$, where $R_{bt}$ is pneumatic impedance of the flowmeter and $f^*$ is determined by:
   selecting of a fragment of said flow spike waveform data represented by a flow-volume or a logarithm of flow-time relation on an interval between peak flow and a point before the end of the post-occlusion flow spike where flow still significantly exceeds quiet exhalation flow; and
   assigning value of an interception of a tangent line of said fragment with a vertical axis of said flow or logarithm of flow to $f^*$.

5. The method of claim 4 wherein said fragment of said flow spike waveform data represented by either flow-volume or ln(flow)-time waveforms is a part of said flow spike waveform with relatively constant non-zero slope following parts of said flow spike waveform with zero slope corresponding to said peak flow and a subsequent part with a maximum absolute value of slope.

6. The method of claim 1 wherein said determining comprises determining airway resistance of small airways, and said airway resistance of small airways is determined using a level of bending or inflection in said flow spike waveform following peak flow, said flow spike waveform being represented by a flow-volume or a logarithm of flow-time relation.

7. The method of claim 1 wherein said method is repeated as several single exhalation trials, further comprising averaging said at least one of airway resistance and lung compliance determined for each exhalation trial.

8. The method of claim 1 wherein said exhalation trials are excluded under any one of the following conditions:
   a duration of occlusion stage is less than predetermined time;
   said flow spike waveform shows increase of flow after peak flow; and
   said flow spike waveform shows a peak flow significantly higher than peak flow measured at other ones of said exhalation trials.

9. The method of claim 1 wherein said predetermined shutter opening threshold is a level of pressure established by relaxation of breathing muscles in said subject performing quiet exhalation.

10. The method of claim 1 wherein the shutter is released automatically.

11. The method of claim 10 wherein the shutter is released when pressure in the flowmeter exceeds a predetermined threshold.

12. The method of claim 10 wherein the shutter is released when a rate of pressure increase in the flowmeter drops below a threshold indicative of equalization of alveolar and mouth pressure.

13. The method of claim 1 wherein the shutter is attached to a distal end of the flowmeter.

14. The method of claim 1 wherein said recording flow in said flowmeter comprises recording data for up to 200 ms after peak flow.

15. The method of claim 14, wherein said airway resistance is determined for upper airways and upper part of the central airways from maximum air pressure measured before said shutter opening and peak flow and said airway resistance is determined for total of upper airways and lower airways from maximum air pressure measured before said shutter opening and flow value from said flow spike waveform data.

16. The method of claim 1, further comprising said device identifying when said subject's exhalation into said flowmeter was performed with applying forced efforts, wherein said identifying comprises one of: monitoring said detected air pressure during said occluding; and analysing said measured flow data representing said post-occlusion flow.

17. An apparatus for determining at least one of airway resistance and lung compliance during quiet exhalation, the apparatus comprising a mouthpiece, a flow tube, a shutter for occluding exhalation flow in the flow tube during initial exhalation when closed and for allowing flow through the flow tube when open, at least one sensor for measuring pressure in the flow tube when the shutter is closed and exhalation flow through the flow tube when the shutter is open, a processor and a non-transitory computer-readable memory storing processor instructions to perform the method of claim 1.

18. The apparatus of claim 17, wherein said shutter is controlled to be released by said processor.

19. The apparatus of claims 18 comprising a first device with said mouthpiece, said flow tube, said shutter and said at least one sensor, said first device further comprising a wireless coupling connected to said shutter and said at least one sensor, and a handheld computer in connection with said first device through said wireless coupling, said handheld computer having said processor and said non-transitory computer-readable memory.

20. A non-transitory computer-readable memory storing said processor instructions for use with said handheld computer forming part of the apparatus of claim 19.

* * * * *